United States Patent [19]
Cabilly et al.

[11] Patent Number: 5,582,702
[45] Date of Patent: Dec. 10, 1996

[54] APPARATUS AND METHOD FOR ELECTROPHORESIS

[75] Inventors: Shmuel Cabilly, Gedera; Uri Yogev, Herzelia, both of Israel

[73] Assignee: Ethrog Biotechnology Ltd., Israel

[21] Appl. No.: 427,917

[22] Filed: Apr. 26, 1995

[51] Int. Cl.⁶ .................................................. G01N 27/26
[52] U.S. Cl. ......................... 204/456; 204/465; 204/606; 204/612; 204/615
[58] Field of Search ........................... 204/182.8, 299 R, 204/456, 465, 606, 615, 612

[56] References Cited

U.S. PATENT DOCUMENTS

| | | | |
|---|---|---|---|
| 4,323,439 | 4/1982 | O'Farrell | 204/182.8 |
| 4,874,491 | 10/1989 | Stalberg | 204/182.8 |
| 4,892,639 | 1/1990 | Sarrine et al. | 204/299 R |
| 5,045,164 | 9/1991 | Tansamrit et al. | 204/182.8 |
| 5,209,831 | 5/1993 | MacConnell | 204/299 R |
| 5,407,552 | 4/1995 | Lebacq | 204/299 R |
| 5,411,657 | 5/1995 | Leka | 204/299 R |

*Primary Examiner*—Arun S. Phasge
*Attorney, Agent, or Firm*—Skjerven, Morrill, MacPherson, Franklin & Friel LLP; Forest E. Gunnison

[57] ABSTRACT

A substantially closed cassette for conducting therein electrophoresis separation which includes a closed chamber, the chamber includes therein a body of gel, means for providing ions for driving the electrophoresis separation and electrodes for connecting the cassette to an external electrical power source, thereby enabling to drive the electrophoresis separation.

32 Claims, 3 Drawing Sheets

APPARATUS AND METHOD FOR ELECTROPHORESIS

FIELD OF THE INVENTION

The present invention relates to electrophoresis generally and more particularly to apparatus for conducting an electrophoresis test therein.

BACKGROUND OF THE INVENTION

A great deal of diagnostic procedures and laboratory research are carried out wherein DNA, RNA or proteins are separated according to their physical and chemical properties via electrophoresis. This process is widely used and has many applications. For example, it is used to analyze DNA molecules according to their resultant size after being digested by restriction enzymes. It is also used to analyze the products of a polymerase chain reaction (PCR).

Typically, electrophoresis separation is carried out in a separation medium, such as a gel of agarose or acrylamide or a combination of the two. Usually, agarose gels are cast in open trays and form a slab whereas acrylamide gels are cast between two glass plates.

In order to effect the electrophoretic separation, two opposite ends of the gels are exposed to an electrically conducting buffer which is connected by electrodes, typically carbon or platinum, to an electric power source. Once the electrical power source is switched on, the electric field forces negatively charged molecules to move towards the anode and positively charged molecules to move towards the cathode. One characteristic of conventional electrophoresis is the use of large volumes of buffer having a relatively low salt concentration to maintain the required electric field.

DNA is negatively charged and therefore, in the agarose or acrylamide gels which provide sieving action, DNA molecules move towards the anode at a rate which depends on their size, wherein the smaller the molecules the faster they move.

Typically, it is desirable to visualize and to document the results of the electrophoresis separation test. In electrophoresis separation of DNA molecules, this has been done by immersing the gel slab after the electrophoretic separation has been completed in a solution of a fluorescent compound which emits visible light when exposed to a ultra violet (UV) light. A widely used compound is ethydium bromide.

Conventional electrophoresis separation systems are deficient in many respects, a few of which are listed below.

Prior art electrophoresis separation systems are a potential source of contamination to the working environment in which the tests are performed. The two major sources of contamination are ethydium bromide and PCR products. Ethydium bromide is a hazardous chemical due to its mutagenic activity and therefore, exposure to ethydium bromide may induce malignant tumors. PCR is an extremely sensitive method to the extent that a single molecule of DNA product from one PCR (out of the trillions of molecules being produced) may interfere with the subsequent PCR such that it will produce incorrect result.

Conventional electrophoresis is also deficient in other respects, one being that it is time consuming.

Various attempts have been made to solve the deficiencies of conventional electrophoresis. Most attempts have been addressed to overcome the deficiency of conventional electrophoresis systems with respect to the use of buffers therein.

U.S. Pat. No. 4,874,491 to Stalberg describes an electrophoresis system having a buffer containing gel.

U.S. Pat. No. 4,892,639 to Sarrine et al. describes an electrophoresis plate with improved buffer circulation.

U.S. Pat. No. 5,045,164 to Aungnapa et al. describes an electrophoresis plate having buffer reservoirs of high concentration to provide the ions required for driving the electrophoresis process.

U.S. Pat. No. 5,209,831 to MacConnel describes a bufferless disposable cassette having open ends and a conductive film which provides the ions provided by the buffer in conventional electrophoresis systems.

SUMMARY OF THE INVENTION

It is therefore an object of the present invention to provide an improved apparatus for electrophoresis.

A major object of the present invention is to provide a closed cassette for electrophoresis.

According to an aspect of the present invention the cassette is a disposable cassette.

The cassette of the present invention overcomes drawbacks associated with prior art electrophoresis cassettes, plates or slabs. Since the cassette is a closed one, its outer environment is not susceptible to contamination. Moreover, since it is ready to use, the preparation time required for preparing prior art cassettes is saved.

Another object of the present invention is to provide an electrophoresis system in which both the electrophoresis separation and the visualization of the results thereof are done while the cassette is in situ.

According to one aspect of the present invention, there is provided a substantially closed disposable cassette with openings for introducing a sample of molecules thereinto, the openings being preferably opened only just before the electrophoresis test.

According to another aspect of the present invention, the cassette includes all the chemical compounds required to drive the electrophoretic separation, and, when DNA molecules are separated, the compounds required to stain the separated DNA.

According to a preferred embodiment of the present invention, the ions (cations and anions) required to drive the electrophoretic separation are provided by a cation exchange matrix and an anion exchange matrix, respectively.

According to another preferred embodiment of the present invention, the cation exchange matrix also provides the cations required to stain the separated molecules in order to enable visualization thereof when the cassette is illuminated with a UV light source.

One advantage of the cassette of the present invention is that it is disposable.

Another advantage of the cassette of the present invention is that the user is not exposed to any hazardous chemical constituent, such as ethydium bromide, as in prior art cassettes.

Yet another advantage of the cassette of the present invention is that PCR products are contained within the cassette and are disposed therewith so as to substantially reduce the contamination of the working environment in which the tests are performed.

There is thus provided, in accordance with a preferred embodiment of the present invention apparatus for conducting electrophoresis separation therein which includes a housing having at least bottom and side walls defining a chamber which includes, in contact therebetween, a body of gel, at least one body of ion exchange matrix for providing the ions for driving the electrophoresis separation, and electrodes for connecting the chamber to an external electrical power source, thereby enabling to drive the electrophoresis separation.

Further, in accordance with a preferred embodiment of the present invention, the apparatus includes at least one body of ion exchange matrix includes a body of cation exchange matrix for providing the cations for driving the electrophoresis separation and a body of anion exchange matrix for providing the anions for driving the electrophoresis separation.

Further, in accordance with a preferred embodiment of the present invention, the apparatus also includes a cover for closing the chamber, thereby providing a substantially closed apparatus.

According to a preferred embodiment of the present invention, the cover have at least one opening therein for introducing a test sample into the body of gel.

Additionally, according to a preferred embodiment of the present invention, the openings are closed by a comb like structure prior to the electrophoresis separation.

Further, in accordance with a preferred embodiment of the present invention, the apparatus also includes a buffer solution in contact with the body of gel, the at least one body of ion exchange matrix and the electrodes.

In accordance with a preferred embodiment of the present invention, the cation exchange matrix is disposed at one end of the body of gel and the body of anion exchange matrix is disposed on a second end of the gel.

Further, according to a preferred embodiment of the present invention, at least the cover and the bottom wall are transparent to ultra violet (UV) radiation.

Still further, according to a preferred embodiment of the present invention, the cation exchange matrix exchanges protons derived from electrolysis with the cations for driving the electrophoresis separation and the anion exchange matrix exchanges hydroxyl ions derived from the electrolysis with the anions for driving the electrophoresis separation.

According to one preferred embodiment of the present invention, the cation exchange matrix and the anion exchange matrix includes particles immersed in a support matrix. Preferably, the support matrix is the gel.

In accordance with one preferred embodiment of the present invention, the apparatus includes closed vent holes in the cover, the vent holes being opened when the apparatus is used.

Further, according to a preferred embodiment of the present invention, the buffer is a Tris ($C_4H_{11}NO_3$) Acetate EDTA (Ethylenediamintetraacetic acid) buffer (TAE herein), the cation exchange matrix releases Tris$^+$ cations and the anion exchange matrix releases acetate anions.

Additionally, according to a preferred embodiment of the present invention, the buffer also includes ethydium bromide and the cation exchange matrix also releases ethydium cations.

In accordance with a preferred embodiment of the present invention, the apparatus may be substantially flat and may be disposable.

There is also provided, in accordance with a preferred embodiment of the present invention, a substantially closed cassette for conducting therein electrophoresis separation which includes a closed chamber which includes therein a body of gel, means for providing ions for driving the electrophoresis separation, and electrodes for connecting the cassette to an external electrical power source, thereby enabling to drive the electrophoresis separation.

Further, according to a preferred embodiment of the present invention, the chamber having top, bottom and side walls, wherein one of the bottom and top walls is an openable cover.

In accordance with a preferred embodiment of the present invention the top wall includes openings for introducing a test sample into the body of gel.

Further, according to a preferred embodiment of the present invention, the cassette includes a comb like structure for closing the openings.

Still further, according to a preferred embodiment of the present invention, the means for providing ions include at least one ion exchange matrix.

According to a preferred embodiment of the present invention, one of the bottom or top walls include at least one openable vent hole.

Further, according to a preferred embodiment of the present invention, the cassette may be substantially flat and may be disposable.

There is also provided, in accordance with a preferred embodiment of the present invention a system for conducting electrophoresis separation which includes an electrical power source, a substantially closed disposable cassette for conducting an electrophoresis separation therein and having conductive elements therein, and a support for supporting the substantially closed cassette and for connecting the electrical power source to the conductive elements of the cassette.

Further, according to a preferred embodiment of the present invention, the system also includes a UV light source and the cassette is transparent to UV light and includes a UV sensitive material capable of interacting with the molecules undergoing electrophoresis separation and of emitting light, thereby enabling to conduct the electrophoresis separation and to visualize it while the cassette is in situ. Preferably, the UV sensitive material is ethydium bromide.

According to a preferred embodiment of the present invention, the system may include a camera, preferably a video camera, for documenting the results of the electrophoresis separation.

According to a preferred embodiment of the present invention, the system may also include a cooling system for cooling the cassette during the electrophoresis test.

Further, according to a preferred embodiment of the present invention, the cassette includes therein at least one ion exchange matrix for providing the UV detectable material.

Finally, there is provided, in accordance with a preferred embodiment of the present invention an electrophoresis method which includes the steps of providing a test sample in a gel, applying an electrical field to the gel, and driving an electrophoresis separation by providing ions required therefor by at least one ion exchange material.

BRIEF DESCRIPTION OF THE DRAWINGS

The present invention will be understood and appreciated more fully from the following detailed description taken in conjunction with the appended drawings in which.

DETAILED DESCRIPTION OF THE PRESENT INVENTION

Reference is now made to FIGS. 1–4 which illustrate an electrophoresis disposable cassette, generally referenced 10, constructed and operative in accordance with a preferred embodiment of the present invention.

Figure 1:
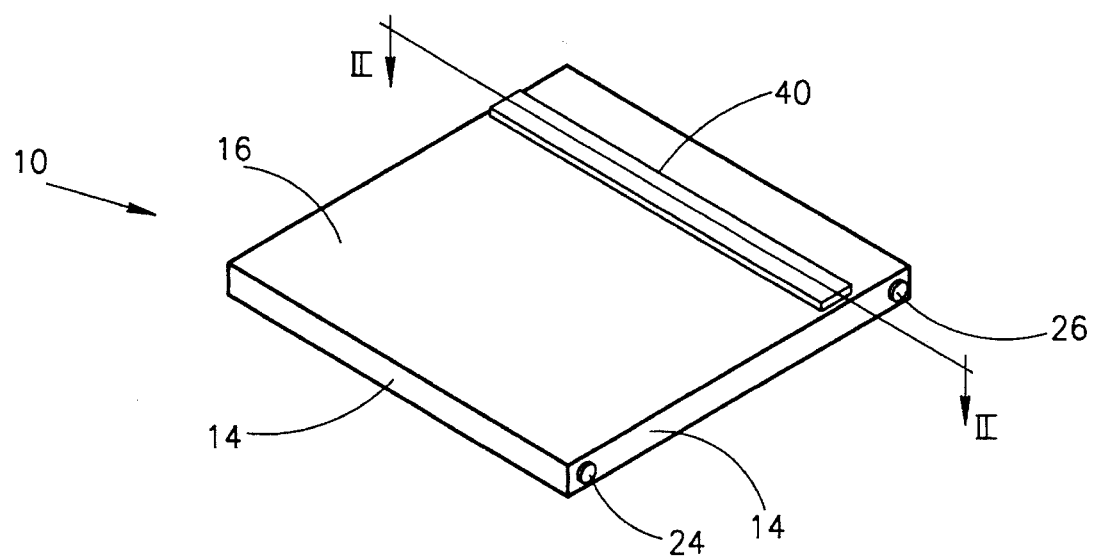
FIG. 1 is a schematic isometric illustration of an electrophoresis cassette, constructed and operative in accordance with a preferred embodiment of the present invention.

The cassette 10, as best seen in FIG. 1, is a closed disposable cassette used for a single electrophoresis test. The cassette 10 includes all the chemical compounds required for driving the electrophoresis separation and for enabling visualization of its results when DNA as well as RNA or protein molecules have been separated.

It will be appreciated that while the cassette 10 is described with respect to electrophoresis separation of DNA molecules, it may be used for electrophoresis separation of any suitable molecules, such as RNA molecules and proteins, mutatis mutandis.

Figure 3:
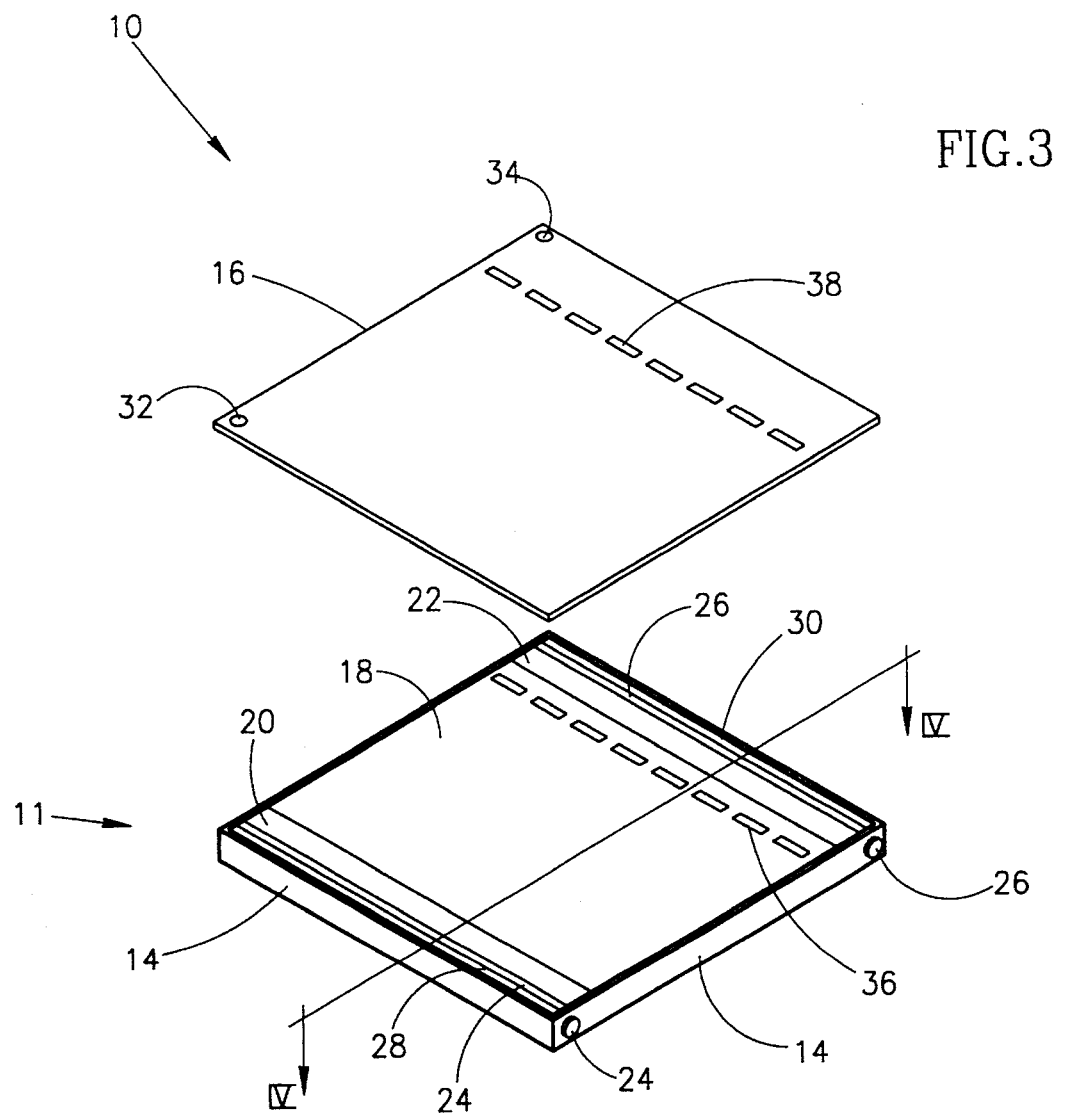
FIG. 3 is a schematic isometric exploded illustration of the cassette of FIG. 1.

As best seen in FIG. 3, the cassette 10 preferably comprises a three dimensional chamber 11 which is preferably substantially flat, having bottom wall and side walls, referenced 12 and 14 respectively, and a cover 16 which forms the top wall of the cassette. The bottom wall 12 (FIG. 4) and the cover 16 are preferably made of any suitable UV transparent material, such as the TPX plastic commercially available from MITSUI of Japan or the PMMA plastic, commercially available form Repsol Polivar S.P.A. of Rome, Italy.

Figure 4:
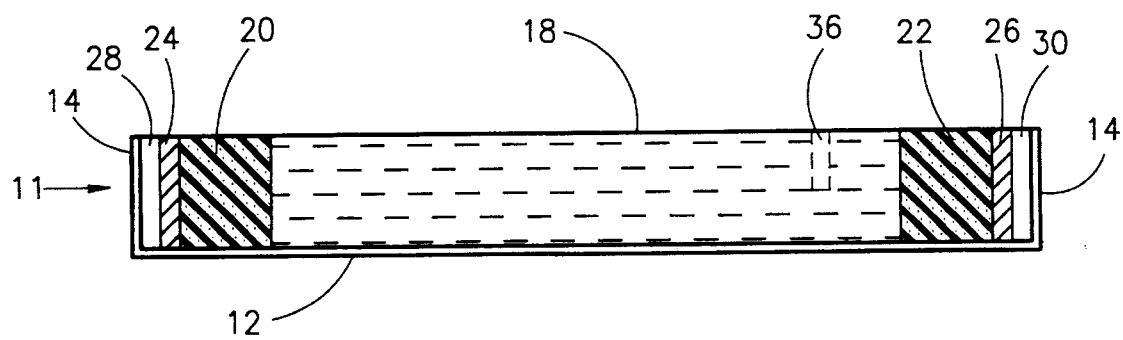
FIG. 4 is a schematic cross section illustration along lines IV—IV in FIG. 3.

As best seen in the cross section illustration of FIG. 4, chamber 11 preferably comprises a gel matrix 18 which may be any suitable gel matrix for electrophoresis, such as an agarose gel or a gel made of acrylamide, a cation exchange matrix 20 and an anion exchange matrix 22, collectively referred to as the ion exchange matrices 20 and 22. The chamber 11 preferably also comprises two conductive rods referenced 24 and 26, such as stainless steel rods which, when connected to an external direct current (DC) electrical power source, provide the electric field required to drive electrophoretic separation. In the illustrated embodiment, rod 24 is the anode and rod 26 is the cathode. Chamber 11 further comprises two unoccupied internal volumes 28 and 30, in which gases produced during the electrophoresis test may accumulate. Alternatively, the open cover 16 may include two vent holes 32 and 34, shown only in FIG. 3, for venting the gases accumulated in the volumes 28 and 30.

It will be appreciated that if the cassette 10 includes vent holes 32 and 34 they are opened just before the electrophoresis tests begins and are closed after the test is completed to substantially reduce the possibility of contamination originated therefrom.

Preferably, each of the gel 18, the ion exchange matrices 20 and 22 and the conductive rods 24 and 26 are in contact and are immersed in a relatively small amount of a buffer solution, such as a TAE buffer, which facilitates the mobility of the molecules undergoing separation and of the ions provided by the ion exchange matrices 20 and 22.

It is a particular feature of the present invention that the ions required for driving the electrophoretic separation are provided by the ion exchange matrices 20 and 22, preferably, by exchanging with protons and hydroxyl ions derived from electrolysis of $H_2O$.

The cation exchange matrix 20 and the anions exchange matrix 22 release the cations and anions required for driving electrophoresis separation. An example of a suitable cation is the $Tris^{(+)}$ cation and an example of a suitable anion is $acetate^{(+)}$. Preferably, but not necessarily, the ions released by the ion exchange matrices 20 and 22 are exchanged with absorbed protons and hydroxyl anions, respectively. Alternatively, or in addition thereto, the ions absorbed by the ion exchange matrices 20 and 22 may also be provided by the rods 24 and 26.

It will be appreciated that the use of the ion exchange matrices 20 and 22 provides a generally uniform pH throughout the cell since any proton buildup near the anode 24 is compensated by absorption thereof by the neighboring cation exchange matrix 20 and hydroxyl buildup near the cathode 26 is compensated by absorption thereof by the anion exchange matrix 22.

According to one preferred embodiment of the present invention, the cation exchange matrix 20 and the anions exchange matrix 22 may be immersed in one of the materials used for preparing the gel.

A suitable cation exchange material is the CM-25-120 Sephadex and a suitable anion exchange material is the WA-30, both of which are commercially available from Sigma Inc. of St. Louis, U.S.A.

The cassette 10 preferably also includes wells 36 in the gel 18. The wells 36 are used to introduce samples of the molecules which are to undergo electrophoretic separation. The wells 36 may be formed by any suitable method, such as by introducing a comb like structure 40 (FIG. 2) to the gel during the assembly of the gel. The comb 40 is introduced to the gel via corresponding openings 38 (FIG. 1) in the cover 16. The openings 38 may be used as an additional space for loading the molecular samples just before the onset of the electrophoresis test after the comb 40 is removed.

Figure 2:
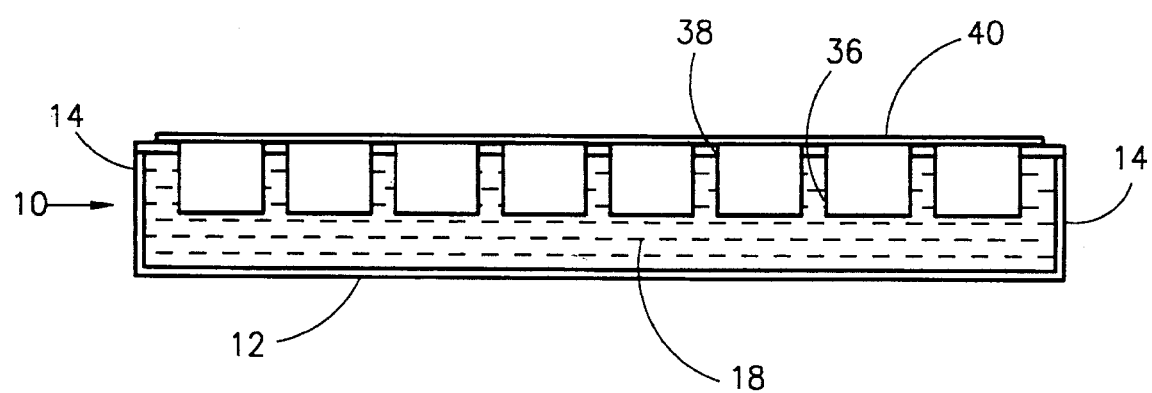
FIG. 2 is a schematic cross section illustration along lines II—II in FIG. 1.

According to a preferred embodiment of the present invention, as best seen from FIG. 2, the wells 36 are covered by the comb 40 used in their preparation. This is since the comb method involves insertion of a comb like structure into the gel via the openings 38 in the top cover 16, the comb being pulled out only just before the electrophoresis test.

It is a particular feature of the present invention that the cassette 10 is a closed cassette covered by the comb 40 which is removed just before the electrophoresis test itself.

The cassette 10 also includes a source for ethydium cations which are used for ultra violet (UV) visualization of the separated DNA molecules. Unlike prior art electrophoresis systems, in which ethydium bromide is introduced after separation of the molecules, typically by immersing the gel containing cassette in an ethydium bromide solution, the cassette 10 includes an ethydium bromide source. Preferably, the cation exchange matrix 20 releases not only the TRIS cations but also ethydium cations which interact with the molecules undergoing electrophoretic separation.

The following example, which is not intended to limit the scope of the present invention, illustrates how the cation exchange matrix 20 and the anion exchange matrix 22 are prepared. The following example is for a cassette whose length, width and height are 100 millimeters (mm), 80 mm and 6 mm, respectively. It will be appreciated that a cassette of these dimensions is substantially flat.

The cation exchange matrix 20 is prepared as follows:

A. About 5 grams of CM-25-120 Sephadex particles were washed using three volumes of TAE solution in a concentration 50 times higher than the concentration of the TAE buffer used during the electrophoresis test (herein X50 TAE solution). In this example, the concentration used in the electrophoresis test itself was 0.04 Molar of Tris Acetate with 0.002 Molar EDTA.

B. The CM-25-120 Sephadex particles were washed by distilled water.

C. Two grams of the washed CM-25-120 Sephadex particles were mixed with 50 milliliter 0.5 X TAE buffer and 5 microliter of ethydium bromide.

D. The mixture was left without agitation for an hour so as to let the CM-25-120 particles to settle.

E. 25 milliliters of the mixture were filtered out so as to obtain a 25 ml solution including the 2 grams CM-25-120 Sephadex particles.

F. The obtained 25 ml mixture including the CM-25-120 Sephadex particles were immersed in a 4 percent agarose gel to obtain the cation exchange matrix 20.

The anion exchange matrix 22 is prepared as follows:

A. About 3 grams of WA-30 particles were washed using three volumes of the 50X solution used to wash the cation exchange particles.

B. The WA-30 particles were washed by distilled water until the measured current in the solution was 0.2 mA (providing a 100 volt source).

C. One gram of the WA-30 particles was immersed in a 4 percent agarose gel to obtain the anion exchange matrix 22.

Figure 5:
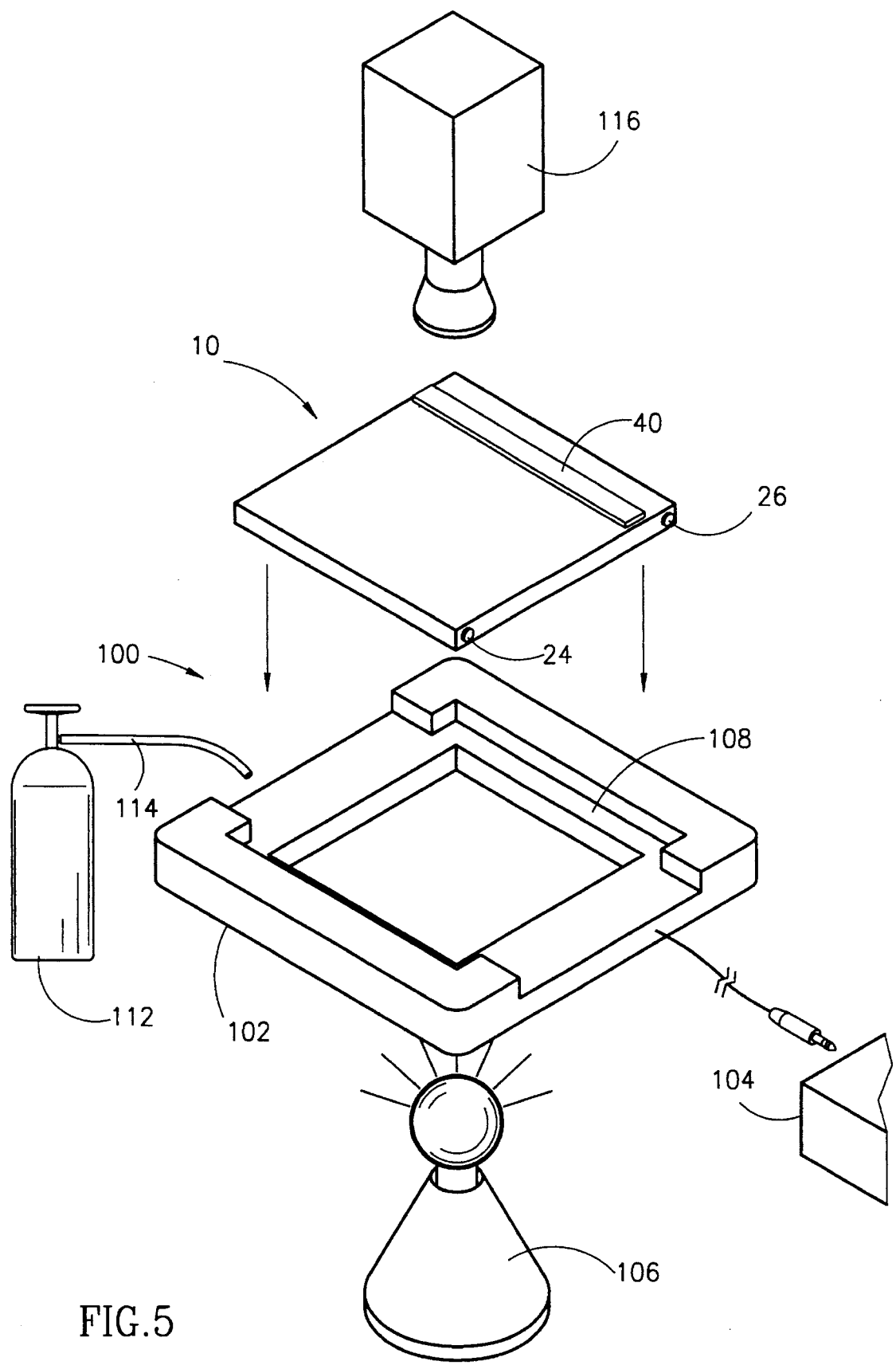
FIG. 5 is schematic isometric illustration of a system for electrophoresis, constructed and operative in accordance with a preferred embodiment of the present invention.

Reference is now made to FIG. 5 which is a schematic isometric illustration of a system for conducting a plurality of electrophoresis tests and which is suitable for visualizing and documenting, in situ, the results thereof, constructed and operative in accordance with a preferred embodiment of the present invention. The system, generally referenced 100, preferably comprises a holder or support housing 102 for supporting the closed disposable cassette 10, a direct current (DC) power source 104 for providing the current required for the electrophoresis process and an ultra violet (UV) light source 106 for illuminating the cassette 10. The holder 102 preferably comprises two connection points (not shown) to which the rods 24 and 26 of the cassette 10 are connected so as to provide thereto the electric field required for the electrophoresis separation.

The system 100 may also comprise means for cooling the cassette 10 during the electrophoresis test, such as a flow of cooled gas, for example, liquid nitrogen, schematically illustrated by the balloon 112 and the tube 114, and means for documenting the electrophoresis separation results, such as a camera, preferably a video camera 116.

It is a particular feature of the system 100 that both the electrophoresis test and the visualization of the results thereof are performed when the cassette 10 is in situ, i.e in the holder 102. Unlike prior art electrophoresis systems for DNA molecules separation where the cassette is taken and immersed in a UV sensitive marker, typically ethydium bromide, after the test, the cassette 10 includes an ethydium bromide source as described with reference to FIGS. 1–4 hereinabove.

In the embodiment illustrated in FIG. 5, the holder 102 is a stand alone open box-like construction which includes a support surface 108 on which the cassette 10 is placed. Alternatively, it may include a UV transparent bottom surface.

Another particular feature of the system 100 is that relatively few number of operations are required from the user in order to conduct an electrophoresis test in the cassette 10. These steps, for electrophoresis separation of DNA molecules include:

A. A sample which includes the DNA molecules to be separated is introduced in the wells 36 of the cassette 10;

B. The electrical current is switched on;

C. If it is desired to expedite the separation the cooled gas flow is also used;

D. As a result of the steps A and B or A, B and C, both electrophoresis separation and interaction of UV detectable compound with the separated DNA molecules take place at the same time.

E. The UV lamp 106 is turned on to visualize the results of the separation. The results may be also recorded by the video camera 116; and F. The user disposes the cassette 10.

It will be appreciated that the preferred embodiments described hereinabove are described by way of example only and that numerous modifications thereto, all of which fall within the scope of the present invention, exist. For example, the ion exchange matrices 20 and 22 of the closed cassette 10 may be replaced with an alternative source of ions such as an internal reservoir of ions in high concentration within capsules which are broken just before the onset of the electrophoresis test.

It will be appreciated by persons skilled in the art that the present invention is not limited to what has been particularly shown and described hereinabove. Rather, the scope of the present invention is defined only by the claims that follow:

We claim:

1. Apparatus for conducting electrophoresis separation therein, the apparatus comprising:

a housing having at least bottom and side walls defining a chamber, said chamber comprises, in contact therebetween:

a body of gel for carrying therein said electrophoresis separation;

at least one body of ion exchange matrix for providing ions for driving said electrophoresis separation; and electrodes for connecting said chamber to an external electrical power source, thereby enabling to drive said electrophoresis separation.

2. Apparatus according to claim 1 wherein said at least one body of ion exchange matrix comprises:

a body of cation exchange matrix for providing the cations for driving said electrophoresis separation; and a body of anion exchange matrix for providing the anions for driving said electrophoresis separation.

3. Apparatus according to claim 2 wherein said cation exchange matrix is disposed at one end of said body of gel and said body of anion exchange matrix is disposed on a second end of said gel.

4. Apparatus according to claim 2 wherein said cation exchange matrix exchanges protons derived from electrolysis with the cations for driving said electrophoresis separation and said anion exchange matrix exchanges hydroxyl ions derived from said electrolysis with the anions for driving said electrophoresis separation.

5. Apparatus according to claim 2 wherein said cation exchange matrix and said anion exchange matrix comprises particles immersed in a support matrix.

6. Apparatus according to claim 5 wherein said support matrix comprises said gel.

7. Apparatus according to claim 1 and also comprising a cover for closing said chamber, thereby providing a substantially closed apparatus.

8. Apparatus according to claim 7 wherein said cover have at least one opening therein for introducing a test sample into said body of gel.

9. Apparatus according to claim 8 wherein said openings are closed by a comb structure prior to the electrophoresis separation.

10. Apparatus according to claim 7 wherein at least said cover and said bottom wall are transparent to ultra violet (UV) radiation.

11. Apparatus according to claim 7 and also comprising closed vent holes in said cover, said vent holes being opened when the apparatus is used.

12. Apparatus according to claim 7 wherein said apparatus is substantially flat.

13. Apparatus according to claim 1 and also comprising a buffer solution in contact with said body of gel, said at least one body of ion exchange matrix and said electrodes.

14. Apparatus according to claim 13 wherein said buffer is a TAE buffer, said cation exchange matrix releases Tris cations and said anion exchange matrix releases acetate anions.

15. Apparatus according to claim 14 wherein said buffer also comprises: ethydium bromide and said cation exchange matrix also releases ethydium cations.

16. Apparatus according to claim 1 wherein said apparatus is disposable.

17. A substantially closed cassette for conducting therein electrophoresis separation comprising:
   a closed chamber which comprises therein:
      a body of gel for carrying therein said electrophoresis separation;
      at least one body of ion exchange matrix for providing ions for driving said electrophoresis separation; and
      electrodes for connecting said cassette to an external electrical power source, thereby enabling to drive said electrophoresis separation.

18. A cassette according to claim 17 wherein said chamber having top, bottom and side walls, wherein one of said bottom and top walls is an openable cover.

19. A cassette according to claim 18 wherein said top wall includes at least one openable vent hole.

20. A cassette according to claim 17 wherein one of said bottom and top walls includes openings for introducing a test sample into said body of gel.

21. A cassette according to claim 20 and further comprising a comb structure for closing said openings.

22. A cassette according to claim 17 wherein said means for providing ions comprises at least one ion exchange matrix.

23. A cassette according to claim 17 wherein said cassette is substantially flat.

24. A cassette according to claim 17 wherein said cassette is disposable.

25. A system for conducting electrophoresis separation comprising:
   an electrical power source;
   a substantially closed disposable cassette for conducting an electrophoresis separation therein and having conductive elements therein, said cassette comprising therein a body of gel for carrying therein said electrophoresis separation and at least one body of ion exchange matrix for providing ions for driving said electrophoresis separation; and
   a support for supporting said substantially closed cassette and for connecting said electrical power source to said conductive elements of said cassette.

26. A system according to claim 25 and wherein said system also comprising a UV light source and wherein said cassette is transparent to UV light and comprises a UV sensitive material capable of interacting with the molecules undergoing electrophoresis separation and of emitting light, thereby enabling to conduct said electrophoresis separation and to visualize it while said cassette is in situ.

27. A system according to claim 26 wherein said UV sensitive material is ethydium bromide.

28. A system according to claim 26 wherein said cassette includes therein at least one ion exchange matrix for providing said UV detectable material.

29. A system according to claim 25 and also comprising camera means for documenting the results of said electrophoresis separation.

30. A system according to claim 25 and also comprising a cooling system for cooling said cassette during said electrophoresis test.

31. An electrophoresis method comprising the steps of:
   introducing a test sample into a body of gel;
   applying an electrical field to said gel; and
   driving an electrophoresis separation by providing ions required for driving said electrophoresis separation by at least one ion exchange matrix.

32. A method for producing a substantially closed cassette for conducting electrophoresis separation therein comprising:
   providing a housing having bottom and side walls defining an open chamber;
   assembling within said chamber in contact therebetween a body of gel for carrying therein said electrophoresis separation, at least one body of ion exchange matrix for providing ions for driving said electrophoresis separation and electrodes for connecting said chamber to an external electrical power source; and
   closing said open housing with a cover, thereby forming a substantially closed cassette capable of carrying electrophoresis separation therein.

* * * * *